(12) United States Patent
Batista et al.

(10) Patent No.: US 12,419,345 B2
(45) Date of Patent: Sep. 23, 2025

(54) AEROSOL GENERATING ARTICLE FOR PROVIDING AN ELECTRICAL STIMULATION TO A USER

(71) Applicant: Philip Morris Products S.A., Neuchatel (CH)

(72) Inventors: Rui Nuno Batista, Neuchatel (CH); Ricardo Cali, Mannheim (DE); Toney Moses Rajan, Mannheim (DE)

(73) Assignee: Philip Morris Products S.A., Neuchatel (CH)

( * ) Notice: Subject to any disclaimer, the term of this patent is extended or adjusted under 35 U.S.C. 154(b) by 483 days.

(21) Appl. No.: 18/000,776

(22) PCT Filed: Jun. 8, 2021

(86) PCT No.: PCT/EP2021/065261
§ 371 (c)(1),
(2) Date: Dec. 5, 2022

(87) PCT Pub. No.: WO2021/249991
PCT Pub. Date: Dec. 16, 2021

(65) Prior Publication Data
US 2023/0225392 A1    Jul. 20, 2023

(30) Foreign Application Priority Data
Jun. 8, 2020 (EP) .................................... 20178737

(51) Int. Cl.
*A24F 40/40* (2020.01)
*A24D 1/20* (2020.01)
(Continued)

(52) U.S. Cl.
CPC ................ *A24D 1/20* (2020.01); *A24F 40/20* (2020.01); *A24F 40/40* (2020.01); *A24F 40/57* (2020.01); *A61N 1/36* (2013.01)

(58) Field of Classification Search
CPC ....................................................... A24F 40/44
(Continued)

(56) References Cited

U.S. PATENT DOCUMENTS

| 4,068,672 A * | 1/1978 | Guerra .................... A24F 13/02 131/270 |
|---|---|---|
| 2018/0206553 A1* | 7/2018 | Reevell ................... A24F 40/50 |

(Continued)

FOREIGN PATENT DOCUMENTS

| CN | 107657999 A | 2/2018 | |
|---|---|---|---|
| CN | 111920109 A * | 11/2020 | ............. A24F 13/02 |

(Continued)

OTHER PUBLICATIONS

Warnke F, DE-3312237-A1, English Translation of the Description (Year: 2025).*

(Continued)

*Primary Examiner* — Philip Y Louie
*Assistant Examiner* — Timothey Tuan-Kha Tran
(74) *Attorney, Agent, or Firm* — Oblon, McClelland, Maier &Neustadt, L.L.P.

(57) ABSTRACT

An aerosol-generating article for providing an electrical stimulation to a user is provided, including an aerosol-forming substrate; first and second electrodes; and first and second tipping papers, the first electrode being disposed at a first position of the substrate to provide a first electrical contact to the user, the second electrode being disposed at a second position at a front face of the substrate to provide a second electrical contact to the user, the second position being different from the first position to provide an electrical potential between the first and the second electrodes and to provide an electrical stimulation to the user, the first electrode being accessible for a first region of the mouth that is a first area on a tongue of the user, and the second electrode (Continued)

being accessible for a second region of the mouth of the user that is different from the first region.

9 Claims, 7 Drawing Sheets

(51) Int. Cl.
    *A24F 40/20*      (2020.01)
    *A24F 40/57*      (2020.01)
    *A61N 1/36*      (2006.01)

(58) Field of Classification Search
    USPC .......................................................... 40/44
    See application file for complete search history.

(56) References Cited

U.S. PATENT DOCUMENTS

| | | |
|---|---|---|
| 2019/0045844 A1 | 2/2019 | Reevell |
| 2021/0015167 A1 | 1/2021 | Moloney et al. |

FOREIGN PATENT DOCUMENTS

| | | | | |
|---|---|---|---|---|
| DE | 3312237 A1 * | 10/1984 | ............. | A61N 1/328 |
| RU | 2 590 876 C2 | 7/2016 | | |
| WO | WO-2015150068 A1 * | 10/2015 | ........... | A24B 15/167 |
| WO | WO 2017/153467 A1 | 9/2017 | | |
| WO | WO 2019/185715 A1 | 10/2019 | | |
| WO | WO-2020161328 A1 * | 8/2020 | ............... | A24D 3/18 |

OTHER PUBLICATIONS

Meng Q, CN-111920109-A ,English Translation of the Description (Year: 2025).*
Russian Office Action issued May 31, 2023 in Russian Application No. 2022134477, with English translation, 9 pgs.
Russian Search Report issued Jun. 8, 2021 in Russian Application 2022134477, with English translation, 4 pgs.
Japanese Office Action issued Jan. 4, 2024 in Japanese Application No. 2022-575418, with English translation, 6 pgs.
International Search Report and Written Opinion issued Sep. 8, 2021 in PCT/EP2021/065261, 17 pages.
International Preliminary Report on Patentability Issued May 16: 2022 in PCT/EP2021/065261, 14 pages.
Guillaume Bailly. "Tastr: goûter un liquide sans liquide (ni vapeur) | Vaping Post". Dec. 13, 2017 (Dec. 13, 2017). XP055745000, Retrieved from the Internet: URL:https://fr.vapingpost.com/tastr-gouter-un-liquide-sans-liquide-ni-vapeur/ [retrieved on Oct. 29, 2020] "Tastr, comment ça marche ?"; p. 3, pp. 1-10.

* cited by examiner

AEROSOL GENERATING ARTICLE FOR PROVIDING AN ELECTRICAL STIMULATION TO A USER

The invention relates to an aerosol generating article for providing an electrical stimulation to a user, a holding device for such aerosol generating article, and a holder including such aerosol generating article.

An aerosol generating article can here be understood as a discardable, single use consumable to be used with an electrically heated smoking system that generates aerosol from the aerosol generating article.

For example, WO 2017/153467 A1 discloses an aerosol-generating article comprising an aerosol-forming substrate and a plurality of electrical fuses. The plurality of electrical fuses are spaced apart from each other, each electrical fuse positions proximate a portion of the aerosol-forming substrate. WO 2019/185715 A1 discloses an aerosol generating device for receiving an aerosol generating article, which comprises an electrical circuit comprising a controller for determining a change in an electrical property of the circuit. The change in the electrical property of the circuit is caused by the user interacting with an aerosol generating article received by the device. CN 107 657 999 A relates to an electronic intelligent auxiliary smoking-cessation filter tip and smoking-cessation devices. Further, there is known a device that stimulates the taste buds by non-invasive electric waves, so that the receptors detect the basic tastes according to frequency, heat and temperature, wherein the pulses are sent and modulates by the device.

Aerosol generating articles of the prior art have a number of advantages over conventional cigarettes and cigars, but there is still room for improvement, in particular, providing aromatic notes and flavoring aspects when compared with a standard performance of conventional smoking articles, including conventional cigarettes and cigars.

It is therefore an object of the invention to provide an improved aerosol generating article that provides aromatic notes and flavoring aspects.

The object of the present disclosure is solved by the subject-matter of the independent claims, wherein further embodiments are incorporated in the dependent claims. It should be noted that the aspects of the disclosure described in the following apply to the aerosol generating article for providing an electrical stimulation to a user, the holding device for an aerosol generating article, and the holder including such aerosol generating article.

According to an aspect of the present disclosure, there is provided an aerosol generating article for providing an electrical stimulation to a user. The aerosol generating article comprises an aerosol forming substrate, a first electrode, and a second electrode.

The first electrode is at a first position of the aerosol forming substrate to provide a first electrical contact to the user.

The second electrode is at a second position at a front face of the aerosol forming substrate to provide a second electrical contact to the user, wherein the second position is different from the first position to enable a provision of an electrical potential between the first electrode and the second electrode to provide an electrical stimulation to the user.

The present aerosol generating article may provide aromatic notes and flavoring aspects by providing electrical stimulation to a user's taste buds during consumption. For example, the aerosol generating article can stimulate the taste buds of the tongue of the user via electrical signals. In other words, electrical impulses may be used to provide electrical taste stimulation on the tongue. The stimulation via the electric potential may cause the user to experience a taste of saltiness, bitterness, sour, sweet and/or umami. These stimulations may enhance the user's experience of aromatic notes and flavoring aspects. These electrically generated aromatic notes and flavoring aspects may improve or alter the user's perception of flavor. The electrically induced perception of flavor may resemble the flavor of conventional cigarettes and cigars. Alternatively, the electrically induced perception of flavor may enhance the user's experience by providing a perception of saltiness, bitterness, sour, sweet and/or umami. This enhanced flavor experience may ease the user's transition from conventional cigarettes and cigars to aerosol generating articles.

The simulated taste sensation generated by an electrical stimulation of the taste buds of the tongue of the user can improve the flavor sensed by the user without adding compounds to aerosol generating article. As a result, a required number of ingredients in the aerosol generating article and the costs of the aerosol generating article is not increased. The present aerosol generating article may further allow a specific position of the electrodes to ensure an adequate and ergonomic function.

The aerosol generating article can be understood as a discardable, single use consumable to be used with an electrically heated smoking system that generates aerosol from the aerosol generating article. The aerosol generating article may comprise a mouth end configured to be inserted into a user's mouth. An opposite end of the aerosol generating article may be configured to be inserted into a heated smoking system that generates aerosol from the aerosol generating article. The aerosol generating article may comprise a mouthpiece and an aerosol forming substrate wrapped in at least a tipping paper.

The aerosol forming substrate can be understood as a rod-shaped article, which generates aerosol when being heated. The aerosol forming substrate may be tobacco. The tobacco may be shredded, granular, formed, rolled, corrugated or otherwise processed. The aerosol forming substrate may be herbal or plant material other than tobacco, which may be similarly processed. The aerosol forming substrate may be flavorings such as menthol or eucalyptus, and may be in liquid form or mixed with tobacco or other plant material. During consumption, the aerosol forming substrate is heated, and air flows past or through the aerosol forming substrate, delivering aerosol formed from the heated substrate to the user's mouth and lungs. This aerosol has flavor derived from the aerosol forming substrate. The aromatic notes and flavoring aspects of the aerosol derived from the aerosol forming substrate may be enhanced by electrical stimulation of taste buds in the tongue of a user.

The first electrode and the second electrode are different electrodes. They are positioned at different locations to provide different contact areas for the user. For example, a user may contact the first electrical contact with their tongue. For example, a user may contact the second electrode with another part of their tongue or their lip. The electrodes may be made of an electric conductive material, preferably metal, and more preferably a silver compound.

The front face of the aerosol generating article can be understood as an end surface of the aerosol generating article. The front face may be at the mouth end of the aerosol generating article. The front face may extend essentially perpendicular or angular to a longitudinal direction and/or a lateral surface of the aerosol generating article. The front face may be accessible to a tongue of a user and in particular to a tip of the tongue. This means the electrode at the front face may be at a location where it is touched by the tongue and the taste buds located there, when in use. The electrode may provide an electric potential to the tip of the tongue, which is particularly sensitive for taste sensations (for example, salty tastes).

The lateral surface of the aerosol generating article can be understood as different from the front face of the aerosol generating article. It can be an outer surface of the aerosol generating article extending along the longitudinal direction of the aerosol generating article. The lateral surface can be a circumferential or peripheral surface of the aerosol generating article.

The electrical potential between the first electrode and the second electrode may cause a difference in electric potential between a part of the tongue and another part of the mouth. The difference in electric potential may stimulate the taste buds of the tongue to bring an artificial taste to the tongue to improve the flavor sensation of the user.

In an embodiment, the first electrode is also at the front face of the aerosol forming substrate. Then, both electrodes are at the front face of the aerosol forming substrate. They share the front face. They can be only at the surface of the front face or at least one of the electrodes can further extend around a portion of the lateral surface of the aerosol forming substrate. In the first case, the electrodes together form a disc at the front face. In the second case, the electrodes together form a cap around the front face and a portion of the lateral surface of the aerosol forming substrate. The front face may be accessible to a tongue of a user and in particular to a tip of the tongue. This means both electrodes at the front face may be at a location where they are touched by the tongue and its taste buds, when in use. Both electrodes may provide an electric potential to different spots on the tip of the tongue, which is particularly sensitive for taste sensations (for example, salty tastes).

In another embodiment, the first electrode is on a lateral surface of the aerosol forming substrate. The first electrode may surround at least partially or completely a portion of the lateral surface of the aerosol generating article. The first electrode may be in form of a full or interrupted band or ring around the aerosol forming substrate.

When the first electrode is on the lateral surface of the aerosol forming substrate, it may be accessible to the tongue of the user and in particular to a central area on the tongue. This means the first electrode may be at a location where it is touched by a central part of the tongue, which is different to and "behind" the tip of the tongue, when in use. It may provide electrical stimulation the central part of the tongue and taste buds located there. The first electrode may provide an electric potential to the central area on the tongue to provide a difference in potential between the first electrode at the central area on the tongue and the second electrode at the tip of the tongue. The difference in electrical potential may stimulate the taste buds of the tongue to bring an artificial taste to the tongue. The electrodes may provide an electric potential to different parts of the tongue, which may be sensitive for different taste sensations compared to the tip of the tongue.

When the first electrode is on the lateral surface of the aerosol forming substrate, it may be accessible to a lip of the user. The first electrode may be accessible to a lower lip, an upper lip or both lips of the user. This means the first electrode may be at a location where it is touched by at least a lip of the user, when in use. The first electrode may provide an electric potential to the lip to provide a difference in potential between the first electrode at the lip and the second electrode at the tongue. Only one electrode may provide the electric potential to the taste buds of the tongue, while the other electrode contacts the lip, which might be more sensitive for other sensations, as for example temperature.

Of course, the first electrode can be arranged at the front face and at the lateral surface of the aerosol forming substrate to be accessible to the tongue and to the lip of the user. In all cases, the first and second electrodes may provide a difference in electric potential to different parts of the mouth. A difference in potential between the first electrode and the second electrode may stimulate the taste buds of the tongue to bring an artificial taste to the tongue.

The aerosol forming substrate may further comprise a third electrode accessible for a third region of the mouth, different from the first electrode and the second electrode. As a result, three different body parts of the user may be used for the taste stimulation, as for example the tongue, the upper and the lower lip or a first part of the tongue, a second, different part of the tongue and the lip. This might also intensify the user experience. Of course, the aerosol forming substrate may also comprise even more than three electrodes.

In an embodiment, the first electrode and the second electrode are electrically connectable to an electric power source to provide the electrical potential between the first electrode and the second electrode. In particular, they may be reversibly connectable or connected to an electric power source. The power source may be configured to provide the electrical potential between the first electrode and the second electrode to stimulate the taste buds. The power source may be a battery or a battery pack. It may be rechargeable.

In an embodiment, the electrical potential may be an alternating electrical potential. It may have a frequency in a range of 50 Hz to 1200 Hz, preferably 500 Hz to 700 Hz. Such frequencies may have an apparent effect on human tissues without causing vibrations of the electrode.

In an embodiment, the power source may be configured to provide the electrical potential with a current in a range of 20 µA to 300 µA, preferably 20 µA to 200 µA, more preferably 40 µA to 180 µA, and even more preferably 100 µA to 130 µA. The electrical current may be an alternating electrical current, preferably with steps of 20 µA to provide a distinguishable intensity of the stimulation.

In an embodiment, the first electrode may be electrically connected to a first electrically conductive element extending at least partially along the aerosol forming substrate. The first electrically conductive element may be electrically connected to a first electric terminal arranged at the aerosol forming substrate. The first electric terminal may be electrically connectable to the electric power source. The position of the electric terminal can be at a center of the aerosol generating article to keep the electric terminal with a safety distance to the heating for the aerosol generating article.

In an embodiment, the second electrode may be electrically connected to a second electrically conductive element extending at least partially along the aerosol forming substrate. The second electrically conductive element may be electrically connected to a second electric terminal arranged at the aerosol forming substrate. The second electric terminal may be electrically connectable to the electric power source. Again, the position of the electric terminal can be at a center of the aerosol generating article to keep the electric terminal with a safety distance to the heating for the aerosol generating article.

An electrode may extend substantially perpendicular to a longitudinal extension of the corresponding electrically conductive element. "Substantially" in this context is intended to indicate to those of ordinary skill in the art that the term "perpendicular" is not intended to mean only perfectly perpendicular, but can incorporate ordinary deviations from perfectly perpendicular. Therefore, "substantially perpendicular" in this instance means that the electrode may deviate from ninety degrees from the longitudinal extension of the electrically conductive element by one degree, two degrees, three degrees, four degrees, five degrees, five to ten degrees and up to twenty-five degrees. The term "substantially" is used accordingly throughout this specification. The longitudinal extension of the electrically conductive element may extend substantially perpendicular to a longitudinal extension of the corresponding electric terminal.

The electrodes, electrically conductive elements and/or the electric terminals can be at least partially be made of electrically conductive materials such as conductive polymers, conductive composites, metallic materials and/or the like.

The aerosol generating article may comprise an aerosol forming substrate wrapped in at least a tipping paper and optionally also in a wrap paper. The aerosol generating article may further comprise a mouthpiece arranged at a mouth end of the aerosol generating article and configured to come in contact with a user's mouth. The mouthpiece or plug may also be wrapped in the at least one tipping paper. At the mouth end, the tipping paper may be folded back (towards an opposite, free end) to form a rounded, smooth end. This prevents the longitudinally extending electrically conductive elements and the like from touching and creating discomfort to the user's mouth. The free end or portion of the aerosol generating article may also only comprise the aerosol forming substrate without being wrapped in the at least one tipping paper. The longitudinally extending electrically conductive elements may extend along the aerosol forming substrate and/or at least partially along the at least one tipping paper. The electrically conductive elements may be provided on an interior or an exterior of the tipping paper.

In an embodiment, the aerosol generating article may comprise a first tipping paper and a second tipping paper. The first electric terminal and the second electric terminal may be provided in the first tipping paper. The first electrode and the second electrode may optionally also be provided in the first tipping paper. A heating element, as for example a strip susceptor, may optionally also be provided in the first tipping paper. The first electrically conductive element and the second electrically conductive element may be provided at the second tipping paper.

The first tipping paper and the second tipping paper may be wound together or may be overlapped such that the first electric terminal electrically contacts the first electrically conductive element and the second electric terminal electrically contacts the second electrically conductive element. This means, the two tipping papers can be placed in wound together or overlapped such that the first tipping paper completes the electrical connection with the second tipping paper in such a way that the electric terminals, the electrically conductive elements and/or the electrodes can make physical and electric contact. Consequently, the assembly of the aerosol generating article is very easy and cost efficient.

As a summary, the present aerosol generating article may use electrical impulses with alternating electric potential of varying frequency and/or direct current optionally within a controlled temperature range (see further below) for taste stimulation. Current, frequency and/or temperature alone or in combination may result in a different and improved taste sensations resulting from electrically stimulating the taste buds of the user.

According to another aspect of the present disclosure, there is provided a holding device for an aerosol generating article. The holding device for an aerosol generating article comprises a reception portion, a first electric portion, and a second electric portion. The reception portion is configured to receive an aerosol generating article as described above. The first electric portion and the second electric portion are arranged in the reception portion to electrically contact a first electrode and second electrode of the aerosol generating article.

The reception portion can be a cavity and preferably a tubular cavity to house the aerosol generating article. When the aerosol generating article is inserted in the reception portion, the first electric portion and the second electric portion of the reception portion can be in electrical contact with the first electrode and the second electrode of the aerosol generating article.

In an embodiment, the holding device may further comprise a heating element configured to heat the aerosol generating article to generate an aerosol. The heating element may be arranged at the reception portion. It may be arranged to at least partially surround at least a portion of the aerosol generating article and/or to be inserted into at least a portion of the aerosol generating article. The heating element may be one of more heating units, for example a heating coil, preferably an inductive heating coil, a susceptor strip, a resistive heating element and/or the like. The holding device may comprise an air intake opening. It may be used as an opening for an availability of ambient air for the user aerosol inhalation and/or for cooling the holding device to prevent an overheating.

In an embodiment, the first electric portion and the second electric portion of the reception portion may be in electric connection with an electric power source. The electric power source may be part of the holding device or may be only electrically connected to the holding device. The electric power source may be configured to provide an electrical potential between the first electrode and the second electrode of the aerosol generating article. The electric power source may therefore be electrically connected to the first electrode and the second electrode of the aerosol generating article. In embodiments, the electric power source is a rechargeable battery.

In an embodiment, the electric power source may be additionally configured to provide energy to heat the aerosol generating article to provide an aerosol. The electric power source may therefore be electrically connected to the heating element. This means the electric power source may be the only power source and it can be used to provide an electrical potential between the first electrode and the second electrode as well as to provide energy for heating the aerosol generating article to generate the aerosol. This makes the holding device very efficient and/or allows reducing the number of components. Of course, there can be also two different power sources for heating the aerosol generating article and for providing the electrical potential between the electrodes.

In an embodiment, the holding device may comprise or may be in electrically connected to a control unit. The control unit may be an electronic control unit, which manages an operation of the holding device in terms of energy management, aerosol generation and/or stimulation. The control unit may be configured to control the electric power source. It may control the amount of electrical potential between the first electric portion and the second electric portion of the reception portion and consequently the amount of electrical potential between the first electrode and the second electrode of the aerosol generating article. As a result, the control unit may control an intensity or strength of the electrical stimulation. This may allow adapting the holding device to each and every user. The control unit may be further configured to control the heating element. As a result, the control unit may control a temperature of the aerosol generating article and thereby an aerosolization of the aerosol generating article.

In an embodiment, the holding device may further comprise at least a temperature control element. The temperature control element may be arranged at the reception portion. It may be arranged to at least partially contact the first and second electric portions. The temperature control element may be configured to control a heat transfer between the first and second electric portions and the first and second electrodes of the aerosol generating article. It may be thereby configured to control a temperature of the first electrode and/or the second electrode, which can be in touch with the user. For example, the temperature control device may be a temperature sensor, which senses the temperature at the heating element and is controlled by the control unit. For example, the control unit may stop providing energy from the electric power source if a threshold temperature is measured at the heating element, preventing overheating of the device.

In an embodiment, the temperature control element may be configured to control the temperature of the first and/or second electrodes of the aerosol generating article in a range of 20 to 35 degrees Celsius, preferably 22 to 25 degrees Celsius. This temperature range seems to be very comfortable for the mouth of the user.

The temperature control element can be used to heat the first and/or second electric portions and thereby the first and/or second electrodes of the aerosol generating article to provide a thermal stimulation to the user. The thermal stimulation may further enhance the user experience. The temperature control element can cooperate with the heating element for heating the aerosol generating article to provide the aerosol and/or may comprise an additional heating unit just for heating the first and/or second electric portions.

The temperature control element may additionally or alternatively be used to cool the first and/or second electric portions and thereby the first and/or second electrodes of the aerosol generating article to avoid an uncomfortable heat sensation at the tongue and/or the lip of the user. The temperature control element may therefore comprise at least a heat sink. The heat sink may be a thermoelectric cooler, as for example a micropeltier element.

The temperature control element may allow a heat transfer relative to the first and/or second electric portions and thereby relative to the first and/or second electrodes to cool or heat the first electrode and/or the second electrode. In an embodiment, the temperature control element may be therefore in contact with a housing of the holding device to transfer heat from the reception portion holding the temperature control element via the housing of the holding device to the environment. To provide enough thermal capacity for the heat transfer, the housing of the holding device may be made of a heat-conducting material, which allows dissipating heat energy from the temperature control element to the ambient air. The housing of the holding device may be made of a dense material, which allows storing and dissipating heat energy, as for example, aluminum or ceramic. Additional heat sink materials may be utilized.

In an embodiment, the temperature control element may further comprise a thermo-paste. The thermo-paste may be arranged between the first and/or second electric portions and the housing of the holding device. The thermo-paste may further improve the heat transfer and thereby the heating and/or cooling of the first electrode and/or the second electrode.

In an embodiment, the holding device may further comprise a multi-terminal ring connector module. The multi-terminal ring connector module may be arranged within the holding device. The multi-terminal ring connector module may be arranged in and around an interior circumference of the reception portion. In a cross section, the multi-terminal ring connector module may comprise a plurality of segments. The segments may be arranged together with a cladding. The cladding may be made of polymer, composite, ceramic and/or the like.

In a side view, the plurality of segments form a plurality of electrically conductive elements or tracks that may extend at least partially along the aerosol forming substrate, a tipping paper and/or the aerosol generating article. At least two of these electrically conductive elements may be electrically connected to the first and second electrodes of the aerosol generating article to provide an electric potential from the power source to the user. In particular, a first segment in the cross section forms a first electrically conductive element extending longitudinally and electrically connecting the first electrode. A second segment in the cross section forms a second electrically conductive element extending longitudinally and electrically connecting the second electrode.

In an embodiment, the holding device may further comprise a gyrosensor and a position control unit. The position control unit is configured to select the first electrically conductive element and the second electrically conductive element out of the plurality of electrically conductive elements or tracks based on position data provided by the gyrosensor. An orientation of the holding device with respect to the user's tongue may thereby decide which electrically conductive elements need to be active at a given precise moment. Such information related to orientation and optionally also activation of the specific electrically conductive elements may be processed by means of the position control unit based on a signal from the gyrosensor.

During operation of the holding device, electrically conductive elements of the multi-terminal ring connector may be activated in a perpendicularly opposite manner to a user's tongue. As a result, an upper surface of the tongue may encounter a first electrode of the aerosol generating article, while a lower surface of the tongue may come in contact with a second electrode of the aerosol generating article. In the meantime, the heating element in the holding device may heat the aerosol generating article, for example by an inductive heating process from an electromagnetic field generated by an induction coil. Aerosol is generated which the user can receive through inhalation. During this inhalation, the user can also receive an amount of preferably alternating electric potential on the tongue by the electrodes. The combination of aerosol inhalation and the electric potential may result in an artificial taste experience for the entire smoking experience.

The holding device may be connected to a main unit. The main unit may comprise the electric power source and/or the control unit. The electric power source may be a rechargeable battery with a charging port. The main unit may also have a heat-dissipating housing made of a heat-conducting material, which allows dissipating heat energy from the temperature control element to the ambient air.

The main unit may be a separate component different from the holding device and reversibly connected to the holding device. The main unit and the holding device may be stacked relative to each other, and may be connected by means of a screw connection, snap-fit connection, friction connection, magnetic connection or the like. Alternatively, the main unit and the holding device may be a single piece. Then, the housing of the holding device and the housing of the main unit are the same unitary component.

In an embodiment, the main unit may comprise at least a button, wheel, toggle, sensor and/or other user-input device. In the following, a button is used as an example. The button may serve as an interface for the user to operate the holding device and adjust the stimulation. The button may be configured to activate the heating element for the aerosol generation. The same or another button may be configured to activate an electrical potential between the first and second electric portions. As a result, the button(s) may allow switching the aerosol generator and/or the artificial taste stimulation on and off.

In an embodiment, the button may be further configured to control the amount of electrical potential between the first and second electric portions. As a result, the button may control an intensity of the electrical stimulation and thereby allow an adjustment of the strength of taste simulation.

As a summary, the present holding device for an aerosol generating article may allow a customizable electrical stimulation experience by adjusting a taste intensity. The taste intensity may be controlled by the user and/or a by means of a preset based on a tracked historic usage of the holding device. The present holding device may further allow a proper temperature of the contact areas with the user by means of a temperature control of the electrodes via a heat transfer element that uses a housing of the holding device to dissipate heat.

According to another aspect of the present disclosure, there is provided a holder comprising an aerosol generating article as described above and a holding device as described above. The aerosol generating article is partially inserted into a reception portion of the holding device.

The holder can be understood as a tobacco heating system that receives an aerosol generating article as a rod-shaped article. The aerosol generating article comprises an aerosol generating substrate, which can be tobacco or other suitable substrates in a solid state.

The present holder may allow a taste improvement by electrical stimulation during consumption. It may generate and manage an electrical signal for electrical taste stimulation. The electrical signal is conducted via the aerosol generating article to the mouth and tongue of the user. The aerosol generating article has means to conduct the electrical signal to the mouth and the tongue and means for an electrical and optionally thermal stimulation of the taste buds on the tongue or the lips of the user. When a user experience starts, the aerosol generating article transmits a specific electrical potential and optionally a temperature to the taste buds of the tongue to provide an additional taste sensation, like salty, sour or bitter. The present holder may use a preferably alternating electric potential of varying frequency or direct current or both, optionally within a controlled temperature range, for the taste stimulation.

An airflow through the holder can be understood as follows: The aerosol generating article may be partially inserted into the reception portion of the holding device. Air may be drawn into the holding device by an action of a user sucking on a mouthpiece of the aerosol generating article. The air may be in particular drawn into the holding device through at least an inlet. The air inlet may be in fluid communication with an air flow channel. As a result, the air drawn into the holding device may pass through the at least one air channel. The drawn air may enter an aerosol forming substrate at a distal end of the aerosol generating article. The drawn air may proceed through the aerosol forming substrate, which may be heated to generate the aerosol, and then to the mouthpiece of the aerosol generating article and back to the user.

According to another aspect of the present disclosure, also a method for an electrical stimulation of taste buds of a user is presented. The method for an electrical stimulation of taste buds of a user comprises the following steps, not necessarily in this order:
providing an aerosol generating article as described above, and
activating a power source and thereby providing an electrical potential between a first electrode and a second electrode of the aerosol generating article to stimulate taste buds on a tongue of the user.

The present method for an electrical stimulation of taste buds of a user may allow a better performance in view of aromatic notes and flavoring aspects compared to conventional aerosol generating methods. The aromatic notes and flavoring aspects are improved, because the present aerosol generating article may provide means to electrically stimulate a user's taste during consumption. It has two electrodes that can have a connection to a mouth of the user and can thereby stimulate the taste buds of the tongue via electrical signals.

In use, a user may insert the aerosol generating article into a holding device through an opening on a top side. The aerosol generating article can make physical and electrical contact with the holding device using electric terminals and electrically conductive elements. These physical contacts bring in an electric current to first and second electrodes at the aerosol generating article to generate an artificial taste stimulation for the user during the user experience. The electric terminals, electrically conductive elements and electrodes allow an electrical conduction of electric potential generated by a power source across an aerosol generating article to a user's tongue. The aerosol generating article can also make physical and electrical contact with a heating element provided in the holding device to generate aerosol from the aerosol generating article. The user may activate the system by pressing at least a button and may generate an aerosol from the aerosol generating article for the user experience in combination with an artificial taste stimulation from the electrodes.

Below, there is provided a non-exhaustive list of non-limiting examples. Any one or more of the features of these examples may be combined with any one or more features of another example, embodiment, or aspect described herein.

A. An aerosol generating article for providing an electrical stimulation to a user, comprising:
an aerosol forming substrate,
a first electrode, and
a second electrode,
the first electrode is at a first position of the aerosol forming substrate to provide a first electrical contact to the user, and
the second electrode is at a second position at a front face of the aerosol forming substrate to provide a second electrical contact to the user, wherein the second position is different from the first position to enable a provision of an electrical potential between the first electrode and the second electrode to provide an electrical stimulation to the user.

B. Aerosol generating article according to claim A, wherein the first electrode is also at the front face of the aerosol forming substrate.
C. Aerosol generating article according to claim A, wherein the first electrode is on a lateral surface of the aerosol forming substrate.
D. Aerosol generating article according to one of the preceding claims, wherein the first electrode is accessible for a first region of the mouth, wherein the first region of the mouth is a first area on a tongue of the user, and wherein the second electrode is accessible for a second region of the mouth of the user, wherein the second region is different to the first region.
E. Aerosol generating article according to claim D, wherein the second region of the mouth is a lip of the user.
F. Aerosol generating article according to claim D, wherein the second region of the mouth is a second area on the tongue of the user, which is different to the first area on the tongue.
G. Aerosol generating article according to the preceding claim, wherein the second area on the tongue is a center part of the tongue.
H. Aerosol generating article according to claim D, wherein the first area on the tongue is a tip of the tongue.
I. Aerosol generating article according to one of the preceding claims, wherein the first electrode and the second electrode are electrically connectable to an electric power source to provide the electrical potential between the first electrode and the second electrode.
J. Aerosol generating article according to claim I, wherein the first electrode is electrically connected to a first electrically conductive element extending at least partially along the aerosol forming substrate, wherein the first electrically conductive element is electrically connected to a first electric terminal arranged at the aerosol forming substrate, and wherein the first electric terminal is electrically connectable to the electric power source.
K. Aerosol generating article according to claim I or J, wherein the second electrode is electrically connected to a second electrically conductive element extending at least partially along the aerosol forming substrate, wherein the second electrically conductive element is electrically connected to a second electric terminal arranged at the aerosol forming substrate, and wherein the second electric terminal is electrically connectable to the electric power source.
L. Aerosol generating article according to claims J and K, further comprising a first tipping paper and a second tipping paper,
  wherein the first electric terminal and the second electric terminal are arranged in the first tipping paper,
  wherein the first electrically conductive element and the second electrically conductive element are arranged in the second tipping paper, and
  wherein the first tipping paper and the second tipping paper are wound together in an overlapping manner such that the first electric terminal electrically contacts the first electrically conductive element and the second electric terminal electrically contacts the second electrically conductive element.
M. A holding device for an aerosol generating article, comprising:
  a reception portion,
  a first electric portion, and
  a second electric portion,
  wherein the reception portion is configured to receive an aerosol generating article according to one of the preceding claims, and
  wherein the first electric portion and the second electric portion are arranged in the reception portion to electrically contact a first electrode and second electrode of the aerosol generating article.
N. Holding device according to the preceding claim, wherein the first electric portion and the second electric portion are in electric connection with an electric power source.
O. Holding device according to claim M or N, further comprising a heating element configured to heat the aerosol generating article.
P. Holding device according to one of the claim M to O, further comprising at least a temperature control element, which is arranged at the reception portion and which is configured to control a heat transfer between the reception portion, the first and second electric portions and the first and second electrodes of the aerosol generating article.
Q. Holding device according to the preceding claim, wherein the temperature control element is in contact with a housing of the holding unit to transfer heat from the reception portion via the housing of the holding unit to the environment.
R. Holding device according to one of the preceding claims, further comprising a multi-terminal ring connector module, wherein the multi-terminal ring connector module comprises a plurality of electrically conductive elements, wherein a first electrically conductive elements is electrically connected to the first electrode and a second electrically conductive element is electrically connected to the second electrode.
S. Holding device according to the preceding claim, further comprising a gyrosensor and a position control unit, wherein the position control unit is configured to select the first electrically conductive element and the second electrically conductive element out of the plurality of electrically conductive elements based on position data provided by the gyrosensor.
T. A holder, comprising:
  an aerosol generating article according to one of the claims A to L,
  a holding device according to one of the claims M to S,
  wherein the aerosol generating article is partially inserted into a reception portion of the holding device.
U. A method for an electrical stimulation of taste buds of a user, comprising:
  providing an aerosol generating article according to one of the claims A to L, and
  activating a power source and thereby providing an electrical potential between a first electrode and a second electrode of the aerosol generating article to stimulate taste buds on a tongue of the user.

Examples will now be further described with reference to the figures in which.

Figure 1A:
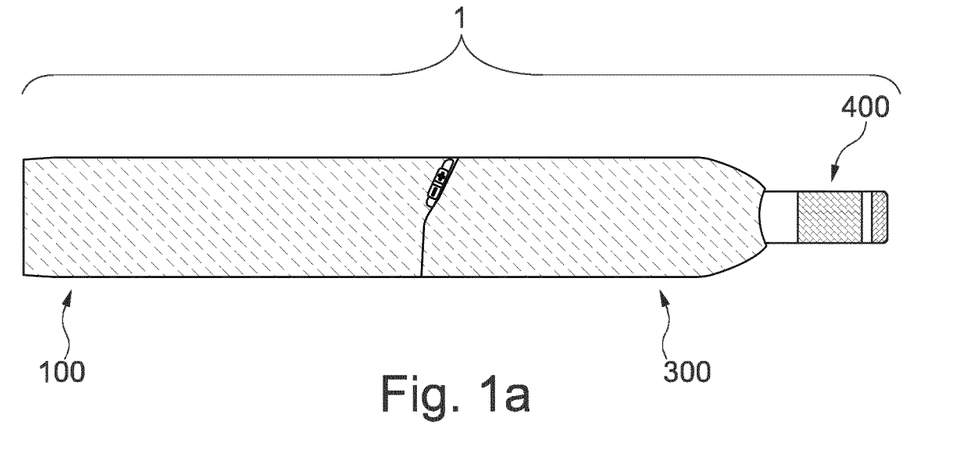
FIG. 1a is a schematic and exemplary view of an embodiment of a holder according to the present disclosure.
Figure 1B:
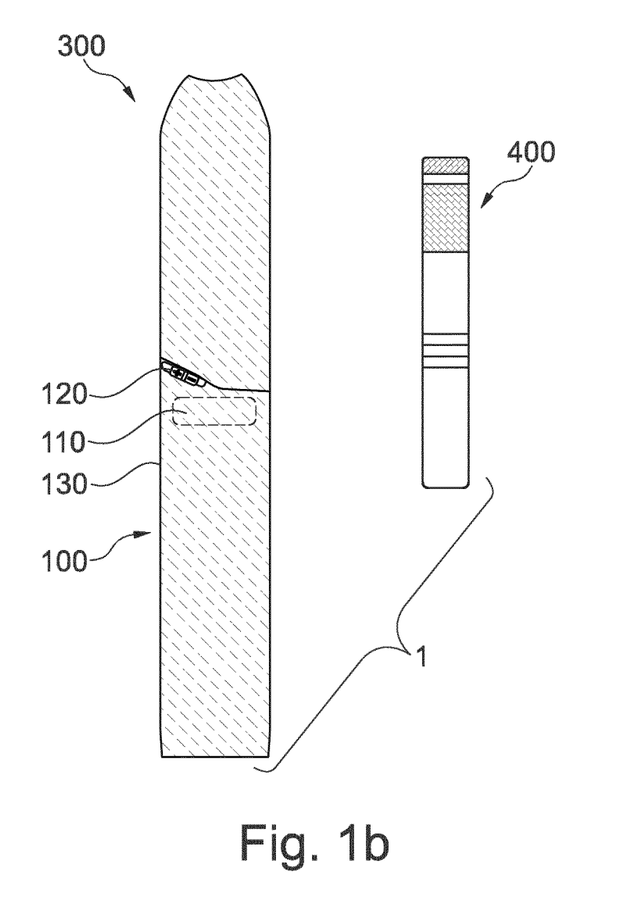
FIG. 1b is a schematic and exemplary view of an embodiment of a holder according to the present disclosure.

FIG. 1a shows a holder 1 with a partially inserted aerosol generating article 400. FIG. 1b shows the holder 1 comprising a holding device 300 for the aerosol generating article 400 and a main unit 100. The aerosol generating article 400 is separate from the holding device 300. The holder 1 comprises the combination of the aerosol generating article 400 and the holding device 300. The holding device 300 is a tobacco heating system that receives the aerosol generating article 400. The aerosol generating article 400 is a rod-shaped article comprising an aerosol generating substrate, which can be tobacco. Details to the aerosol generating article 400 can be found to FIGS. 4 and 5.

The holding device 300 is here reversibly connected to the main unit 100. The main unit 100 has a housing 130, preferably made of a heat-conducting material. The main unit 100 contains and comprises an electric power source (here not shown) and a control unit 110 to supply power to and control a heating element for the aerosol generating article 400 to generate an aerosol to be inhaled. The electric power source and the control unit 110 further supply and control an electrical potential between first and second electrodes of the aerosol generating article 400 for an artificial taste stimulation.

The main unit 100 comprises here a button 120. The button 120 serves as an interface for the user to activate the heating element for the aerosol generating article 400 to generate an aerosol. The button 120 can also be used to activate and control an amount of electrical potential between the first and second electrodes of the aerosol generating article 400 for the artificial taste stimulation.

Figure 2:
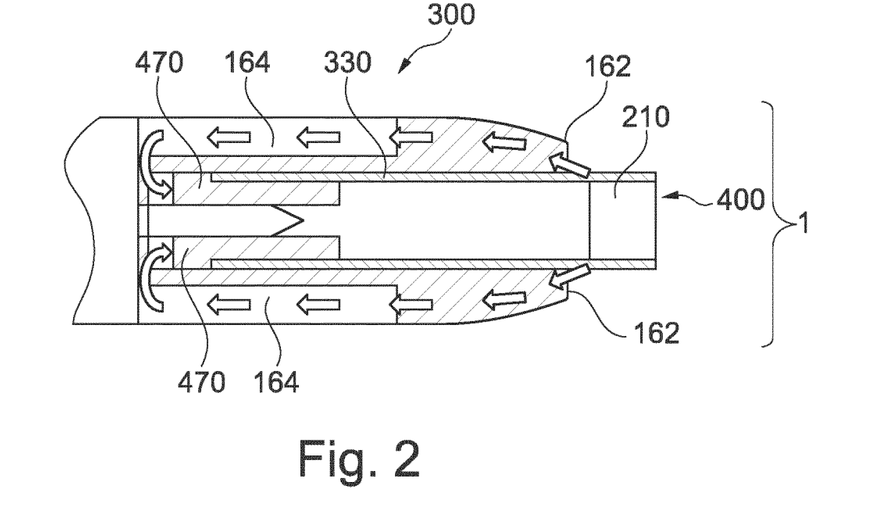
FIG. 2 is a schematic and exemplary cross-section of a holding device according to the present disclosure and an aerosol generating article according to the present disclosure.
Figure 3:
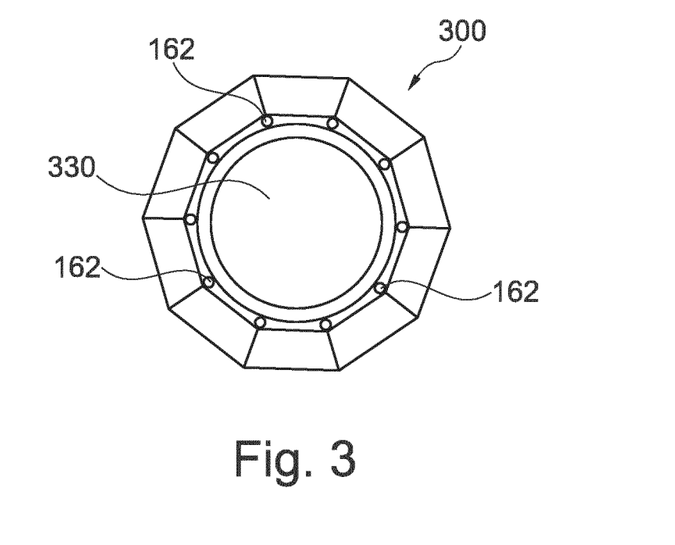
FIG. 3 is a schematic end view of a holding device according to the present disclosure.

FIG. 2 is a schematic cross-section of a holder 1 with a partially inserted aerosol generating article 400. The holder 1 comprises a holding device 300 for the aerosol generating article 400 and a main unit 100 (here not shown). FIG. 3 is a schematic end view of the holding device 300. FIGS. 2 and 3 show a schematic representation of an air flow through a front or proximal end of the holding device 300. The aerosol generating article 400 is received within a reception portion 330 of the holding device 300. Air is drawn into the holding device 300 by an action of a user sucking on a mouthpiece 210 of the aerosol generating article 400. The air is drawn in through inlets 162 in the holding device 300. The air drawn into the holding device 300 passes through air channel(s) 164 around an outside of the reception portion 330. The drawn air enters an aerosol forming substrate 470 at a distal end of the aerosol generating article 400. The drawn air proceeds through the aerosol forming substrate 470, entraining the aerosol, and then to the mouthpiece 210 of the aerosol generating article 400. The air inlets 162 are shown schematically in FIG. 2. There is a plurality of inlets 162 spaced around a circumference of the holding device 300. The inlets 162 are in fluid communication with the air flow channel(s) 164 that surrounds the reception portion 330. The inlets 162 of FIG. 2 are circular but may be any shape. The size and number of inlets 162 may be chosen by the designer and may be chosen to provide a desired resistance to draw through the device.

Figure 4A:
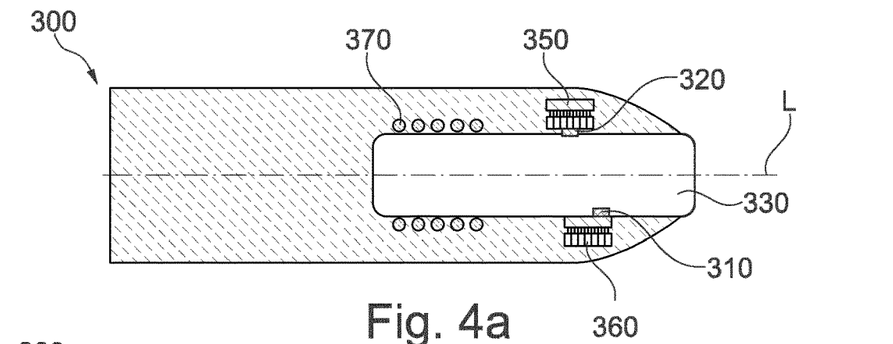
FIG. 4a shows schematically and exemplarily an embodiment of a holding device according to the disclosure.
Figure 4B:
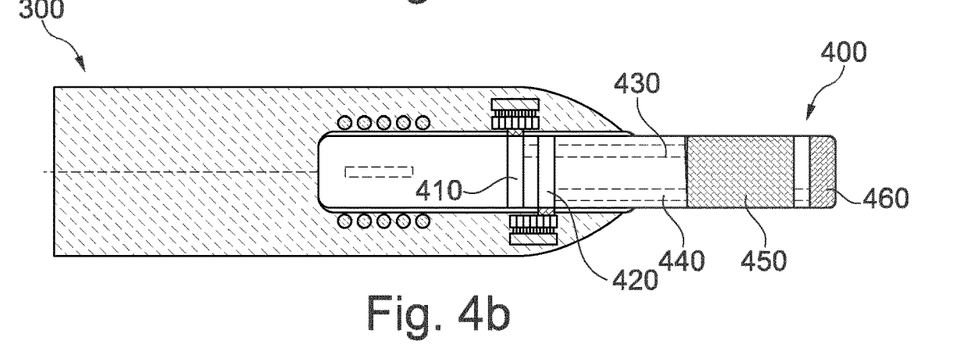
FIG. 4b shows schematically and exemplarily an embodiment of a holding device and an aerosol generating article according to the disclosure.

FIG. 4a is a cross-section of the device shown in FIG. 1b. FIG. 4b is a cross-section of the device shown in FIG. 1a. FIG. 4a shows the holding device 300 according to the present disclosure with a tubular reception portion 330 for the aerosol generating article 400. In FIG. 4a, the reception portion 330 is empty. In FIG. 4b, the aerosol generating article 400 is partially inserted into the reception portion 330. The holding device 300 comprises a heating element 370 arranged around the reception portion 330 for heating the aerosol generating article 400 to generate an aerosol.

The holding device 300 comprises a first electric portion 310 and a second electric portion 320. The first electric portion 310 and the second electric portion 320 are arranged in the reception portion 330. The first electric portion 310 and the second electric portion 320 are electrically connected to the electric power source (not shown).

When the aerosol generating article 400 is inserted in the reception portion 330 (see FIG. 4b), the first electric portion 310 and the second electric portion 320 of the reception portion 330 are in electrical contact with a first electric terminal 410 and a second electric terminal 420 of the aerosol generating article 400. The first electric terminal 410 and second electric terminal 420 make contact with and therefore are electrically connected to a first electrically conductive element 430 and a second electrically conductive element 440 extending along a portion of the aerosol generating article 400 in a longitudinal direction L of the aerosol generating article 400. The first electrically conductive element 430 and the second electrically conductive element 440 make contact with and are therefore electrically connected to a first electrode 450 and a second electrode 460 of the aerosol generating article 400. As a result, the first electrode 450 and the second electrode 460 of the aerosol generating article 400 are electrically connected to the electric power source (not shown).

The holding device 300 comprises two temperature control elements 350, 360. The temperature control elements 350, 360 can be thermoelectric coolers. The temperature control elements 350, 360 are arranged at the reception portion 330 behind and in partial contact with the first and second electric portions 310, 320 of the holding device 300. The temperature control elements 350, 360 control a heat transfer between the environment, the housing 130 of the holding device 300, the first electric portion 310 and second electric portion 320 of the holding device 300, the first electric terminal 410 and second electric terminal 420 of the aerosol generating article 400, the first electrically conductive element 430 and the second electrically conductive element 440 of the aerosol generating article 400 and the first and second electrodes 450, 460 of the aerosol generating article 400. It thereby controls a temperature of the first electrode 450 and the second electrode 460, which are in touch with the user. They might be controlled to a temperature of 20 to 35 degrees Celsius. The temperature control elements 350, 360 can be used to heat and provide a thermal stimulation to the user and/or to cool to avoid an uncomfortable heat sensation at the tongue and/or the lip of the user.

Figure 5A:
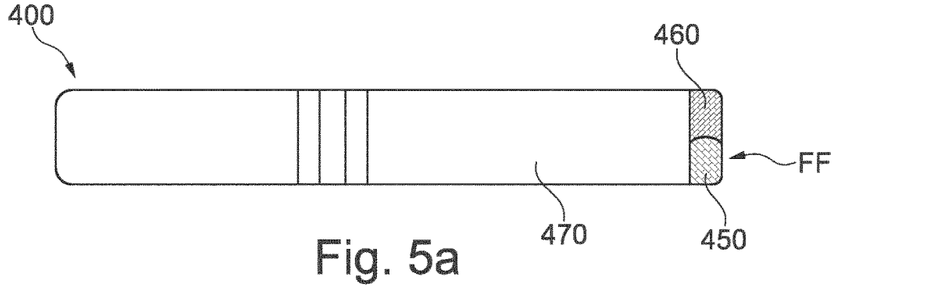
FIG. 5a shows schematically and exemplarily an embodiment of an aerosol generating article according to the disclosure.
Figure 5B:
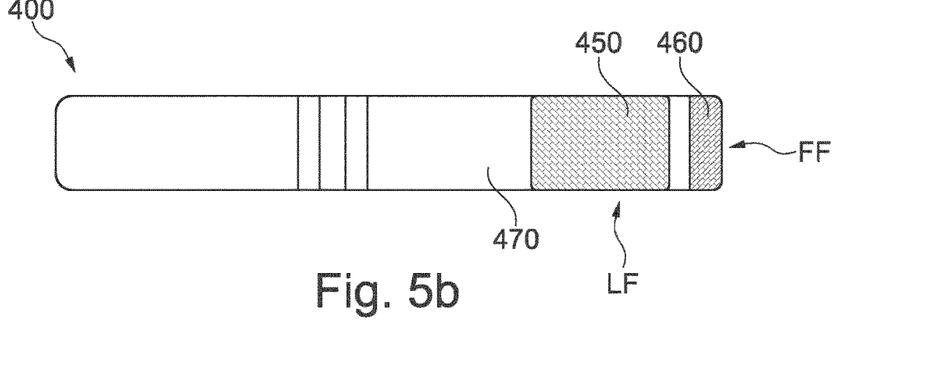
FIG. 5b shows schematically and exemplarily an embodiment of an aerosol generating article according to the disclosure.

FIGS. 5a and 5b show two different embodiments of an aerosol generating article 400 according to the present disclosure. In both cases, the aerosol generating article 400 comprises an aerosol forming substrate 470, a first electrode 450, and a second electrode 460. The first electrode 450 is at a first position of the aerosol forming substrate 470 to provide a first electrical contact to the user. The second electrode 460 is at a second position at a front face FF of the aerosol forming substrate 470 to provide a second electrical contact to the user. The front face FF of the aerosol generating article 400 can be understood as an end surface at a mouth end of the aerosol generating article 400.

The second position is different from the first position. The aerosol generating article 400 enables a provision of an electrical potential between the first electrode 450 and the second electrode 460 to cause a difference in electric potential between a part of the tongue and another part of the mouth. The difference in electric potential may stimulate the taste buds of the tongue to bring an artificial taste to the tongue to improve the flavor sensation of the user.

As shown in FIG. 5a, the first electrode 450 and the second electrode 460 are at a front face FF of the aerosol generating article 400. The first electrode 450 and the second electrode 460 together form a cap around the front face FF and a portion of the lateral surface LF of the aerosol generating article 400. The front face FF may be accessible to a tongue of a user and in particular to a tip of the tongue. This means both electrodes 450, 460 at the front face FF may be at a location where they are touched by the tongue and its taste buds, when in use.

As shown in FIG. 5b, the first electrode 450 is on a lateral surface LF of the aerosol generating article 400 and the second electrode 460 is on the front face FF of the aerosol generating article 400. The lateral surface LF of the aerosol generating article 400 can be understood as an outer, circumferential or peripheral surface of the aerosol generating article 400 extending along a longitudinal direction of the aerosol generating article 400. The first electrode 450 surrounds a portion of the lateral surface of the aerosol generating article 400 like a ring. When the first electrode 450 is on the lateral surface LF of the aerosol generating article 400, it is accessible to the tongue of the user and in particular to a central area on the tongue. This means the first electrode 450 may be touched by a central part of the tongue, which is different to and "behind" the tip of the tongue, when in use. When the first electrode 450 is on the lateral surface LF of the aerosol generating article 400, it is also accessible to a lip and in particular to a lower lip, an upper lip or both lips of the user. This means the first electrode 450 may be touched by at least a lip of the user, when in use.

Figure 6A:
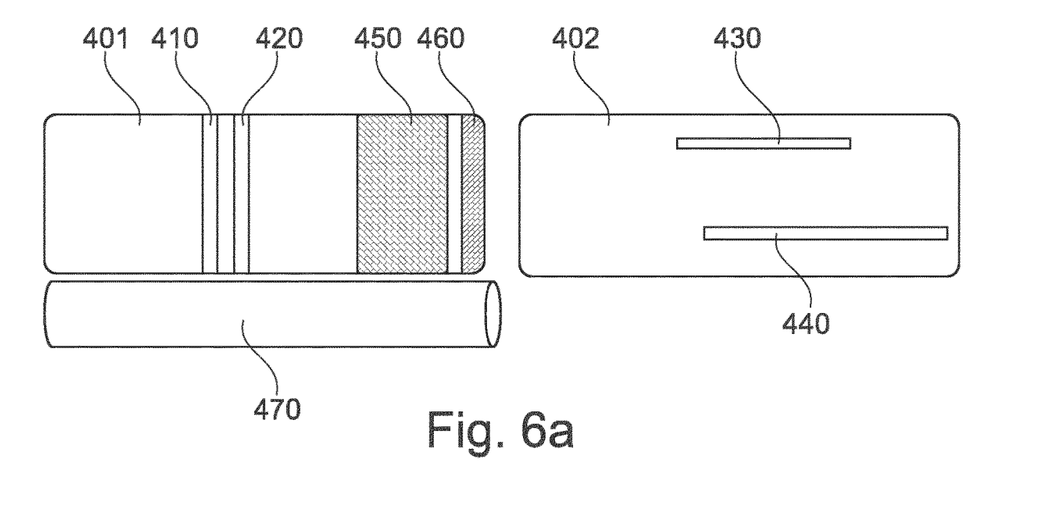
FIG. 6a shows schematically and exemplarily an embodiment of an aerosol generating article according to the disclosure.
Figures 6B, 6C:
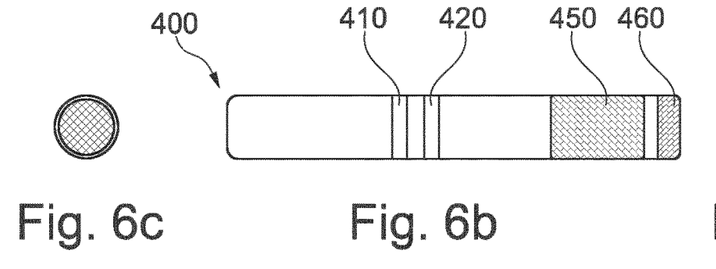
FIG. 6b shows schematically and exemplarily an embodiment of an aerosol generating article according to the disclosure in another perspective.
FIG. 6c shows schematically and exemplarily an embodiment of an aerosol generating article according to the disclosure in another perspective.
Figure 6D:
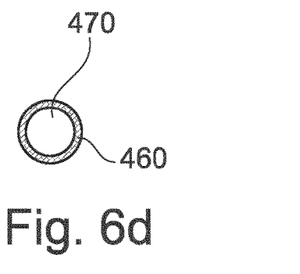
FIG. 6d shows schematically and exemplarily an embodiment of an aerosol generating article according to the disclosure in another perspective.
Figure 6E:
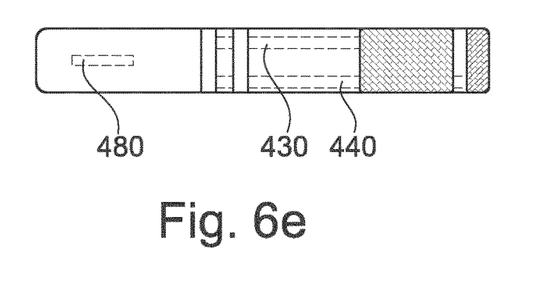
FIG. 6e shows schematically and exemplarily an embodiment of an aerosol generating article according to the disclosure in another perspective.
Figure 7A:
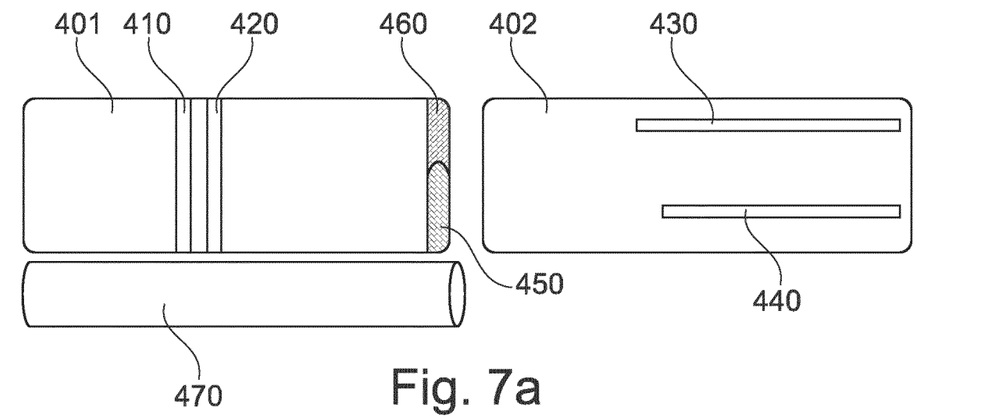
FIG. 7a shows schematically and exemplarily an embodiment of an aerosol generating article according to the disclosure.
Figures 7B, 7C:
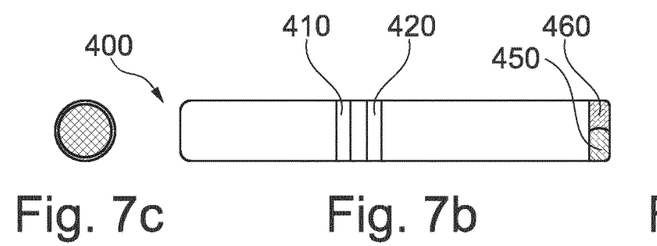
FIG. 7b shows schematically and exemplarily an embodiment of an aerosol generating article according to the disclosure in another perspective.
FIG. 7c shows schematically and exemplarily an embodiment of an aerosol generating article according to the disclosure in another perspective.
Figure 7D:
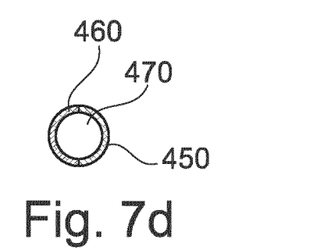
FIG. 7d shows schematically and exemplarily an embodiment of an aerosol generating article according to the disclosure in another perspective.
Figure 7E:
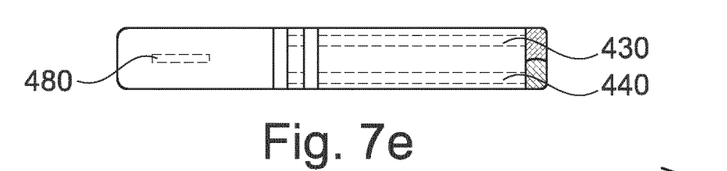
FIG. 7e shows schematically and exemplarily an embodiment of an aerosol generating article according to the disclosure in another perspective.

FIGS. 6a to 6e and 7a to 7e show two different embodiments of an aerosol generating article 400 according to the present disclosure in different perspectives. FIG. 6a shows an explosion view, FIG. 6b a side view, FIG. 6c a top view, FIG. 6d a bottom view and FIG. 6e another side view with inner components marked by dashed lines. Analogue, FIG. 7a shows an explosion view, FIG. 7b a side view, FIG. 7c a top view, FIG. 7d a bottom view and FIG. 7e another side view with inner components marked by dashed lines. The embodiments of FIGS. 6a to 6e and 7a to 7e differ in the arrangement of the electrodes 450, 460 as in FIGS. 5a and 5b. In FIGS. 6a to 6e and 7a to 7e, the aerosol generating article 400 comprises an aerosol forming substrate 470, a first tipping paper 401 and a second tipping paper 402. FIGS. 6a to 6e and 7a to 7e show how the aerosol forming substrate 470 can be wrapped in the tipping papers 401, 402:

The first electric terminal 410 and the second electric terminal 420 are arranged in the first tipping paper 401. The first electrode 450 and the second electrode 460 are also arranged in the first tipping paper 401. A heating element, here for example a strip susceptor 480, is also arranged in the first tipping paper 401.

The first electrically conductive element 430 and the second electrically conductive element 440 are arranged at the second tipping paper 402.

The first tipping paper 401 and the second tipping paper 402 can be wound together in an overlapping manner such that the first electric terminal 410 electrically contacts the first electrically conductive element 430 and the second electric terminal 420 electrically contacts the second electrically conductive element 440. This means, the two tipping papers 401, 402 can be placed in overlapping manner such that the first tipping paper 401 completes the electrical connection with the second tipping paper 402 in such a way that the electric terminals 410, 420, the electrically conductive elements 430, 440 and the electrodes 450, 460 can make physical and electric contact.

Figure 8:
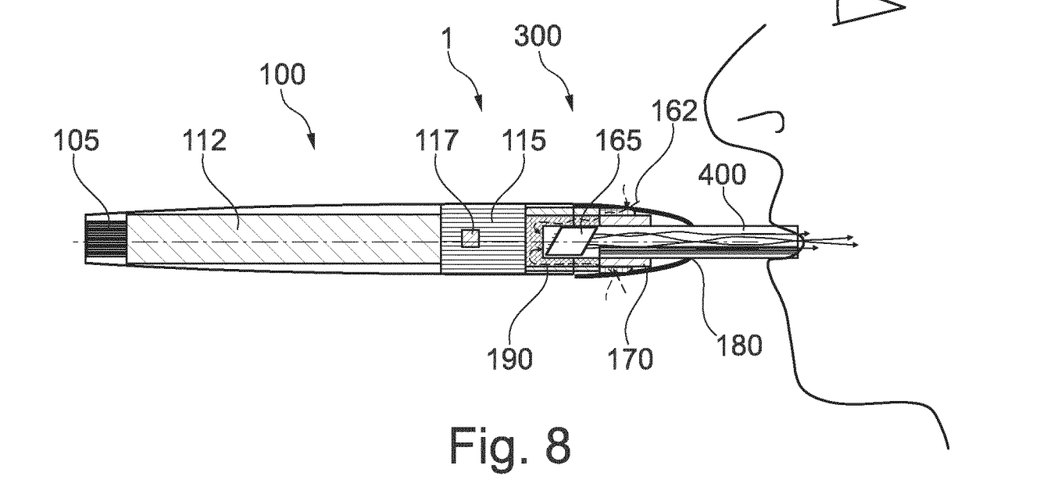
FIG. 8 shows schematically and exemplarily an embodiment of a holder according to the present disclosure.

FIG. 8 shows schematically and exemplarily another embodiment of a holder 1 according to the present disclosure in a cross section. The holder 1 comprises a holding device 300 for an aerosol generating article 400 and a main unit 100. The aerosol generating article 400 is partially inserted into an opening 180 of the holding device 300. The holding device 300 is reversibly connected to the main unit 100.

The main unit 100 comprises an electric power source 112 with a charging port 105 to supply a heating element for the aerosol generating article 400 to generate an aerosol to be inhaled. The heating element here comprises an induction coil 190 and a susceptor 165. The electric power source 112 further supplies an electrical potential between first and second electrodes 450, 460 of the aerosol generating article 400 for an artificial taste stimulation.

The holding device 300 comprises an air intake opening 162, which serves as an opening for an availability of ambient air for a user aerosol inhalation, cools the device exterior and prevents an overheating of the device interiors. The holding device 300 comprises a multi-terminal ring connector module 170 arranged within the holding device 300.

Figure 9A:
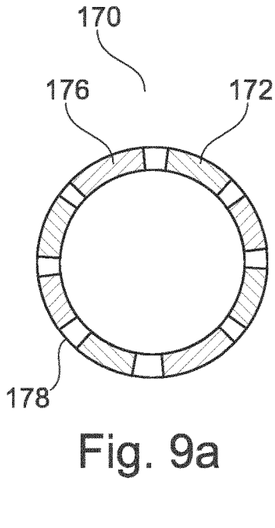
FIG. 9a shows schematically and exemplarily an embodiment of a multi-terminal ring connector module.
Figure 9B:
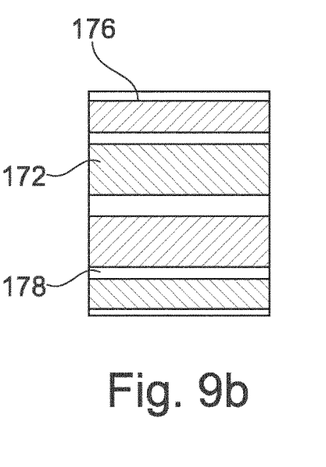
FIG. 9b shows schematically and exemplarily an embodiment of a multi-terminal ring connector module in another perspective.
Figure 9C:
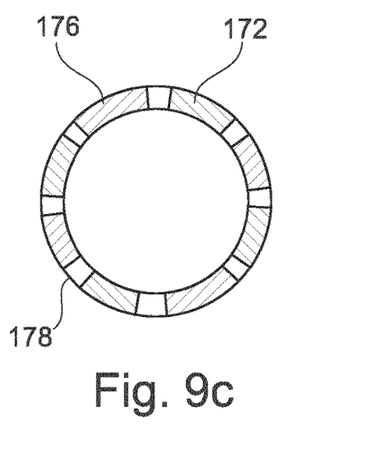
FIG. 9c shows schematically and exemplarily an embodiment of a multi-terminal ring connector module in another perspective.

FIGS. 9a to 9c show schematically and exemplarily an embodiment of the multi-terminal ring connector module 170 in a rear view (FIG. 9a), in a side view (FIG. 9b) and in a front view (FIG. 9c). The multi-terminal ring connector module 170 comprises a plurality of segments 172, 176, which are arranged together with a cladding 178. In the side view in FIG. 9b, the plurality of segments 172, 176 form a plurality of electrically conductive elements 430, 440 or tracks. At least two of these electrically conductive elements 430, 440 can be electrically connected to the first and second electrodes 450, 460 of the aerosol generating article 400 to provide an electric potential from the power source 112 to the user. In particular, a first segment 172 in the cross section forms a first electrically conductive element 430 extending longitudinally and electrically connecting the first electrode 450. A second segment 176 in the cross section forms a second electrically conductive element 440 extending longitudinally and electrically connecting the second electrode 460.

Back to FIG. 8, the holding device 300 comprise a gyrosensor 117 and a position control unit 115. The position control unit 115 selects the first electrically conductive element 430 and the second electrically conductive element 440 out of the plurality of electrically conductive elements or tracks based on position data provided by the gyrosensor 117. An orientation of the holding device 300 with respect to the user's tongue may thereby decide which electrically conductive elements 430, 440 need to be active at a given moment.

In operation, the holding device 300 requires the user to insert an aerosol generating article 400 into the holding device 300. The aerosol generating article 400 passes through the opening 180 towards an interior of the holding device 300 such that the susceptor 165 surrounds the aerosol generating substrate. At the same time, the electrically conductive elements 430, 440 on the aerosol generating article 400 make physical contact with the multi-terminal ring connector module 170.

The multi-terminal connector module is shown in more detail in FIGS. 9a to 9c. The electrically conductive elements 430, 440 make physical contact with segments 172, 176 of the multi-terminal ring connector module 170. These electrically conductive elements 430, 440 allow a conduction of electric potential generated by the electric power source 112 from across the aerosol generating article 400 to the user's tongue. An orientation of the holding device 300 with respect to the user's tongue decides which electrically conductive elements 430, 440 must be active at the given moment. This information related to orientation and activation of the preferred electrically conductive elements 430, 440 gets processed inside the position control unit 115 based on the signals from the gyrosensor 117.

During operation of the holding device 300, two electrically conductive segments 172, 176 of the multi-terminal ring connector 170 are activated, which are arranged at opposite positions on the circumference of the multi-terminal ring connector 170 to touch opposite positions at a user's mouth (not shown in FIGS. 9a to 9c). For example, an upper surface of the tongue meets a first electrically conductive segment, while an upper lip comes in contact with a second electrically conductive segment arranged at an opposite position to the first electrically conductive segment on the circumference of the multi-terminal ring connector 170.

In the meantime, the susceptor 165 in the holding device 300 is heated by an inductive heating process from an electromagnetic field generated by the induction coil 190. This heating of the susceptor 165 heats the aerosol generating substrate resulting in aerosol generation, which the user can receive through the inhalation. During this inhalation, the user can also receive an amount of electric potential on the tongue by the electrodes 450, 460. The combination of aerosol inhalation and the electric potential may result in a taste experience combining aerosol generated from the aerosol generating substrate as well as flavor enhancement from electrical stimulation of the tongue for the entire smoking experience.

Figure 10A:
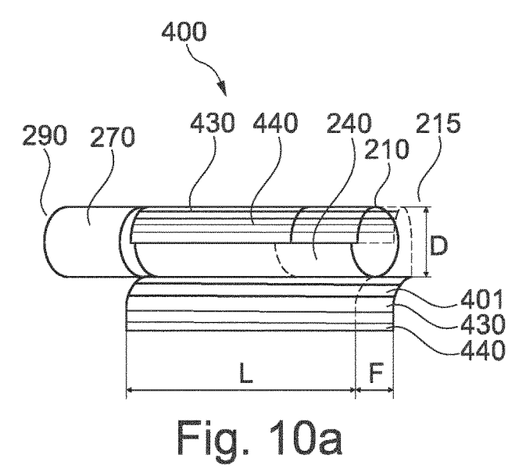
FIG. 10a shows schematically and exemplarily an embodiment of an aerosol generating article according to the disclosure.
Figure 10B:
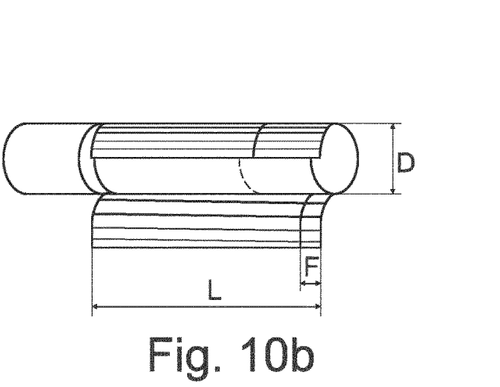
FIG. 10b shows schematically and exemplarily an embodiment of an aerosol generating article according to the disclosure.
Figure 10C:
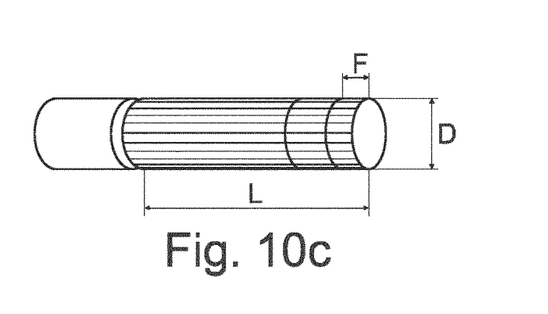
FIG. 10c shows schematically and exemplarily an embodiment of an aerosol generating article according to the disclosure.

FIGS. 10a to 10c show schematically and exemplarily an embodiment of an aerosol generating article 400 according to the disclosure. FIGS. 10a and 10b show the winding and folding of a tipping paper 401, FIG. 10c shows a final form of the aerosol generating article 400.

The aerosol generating article 400 comprises an aerosol forming substrate end 290, an aerosol forming substrate 270, a wrap paper 240, a mouthpiece or plug 210, a plug end 215, and a tipping paper 401 with electrically conductive elements 430, 440. The plug 210 is wrapped with the tipping paper 401 at the plug end 215, which comes in contact with the tongue of the user. The aerosol forming substrate 270 is wrapped with the wrap paper 240 at the aerosol forming substrate end 290 and has no tipping paper over it at the aerosol forming substrate end 290. Between the aerosol forming substrate end 290 and the plug end 215, the tipping paper 401 on the aerosol generating article 400 has parallel electrically conductive elements 430, 440. At the plug end 215, the tipping paper 401 extends forward relative to the plug 210. The tipping paper 401 is folded at the plug end 215, which touches the user's tongue, to keep a surface above the electrically conductive elements 430, 440 at the plug end 215 smooth to prevent wounds on the tongue or lips of the user. 'F' represents a length of a folded area, 'D' represents a diameter of the aerosol generating article 400, and represents a length of the aerosol generating article 400.

Figure 11:
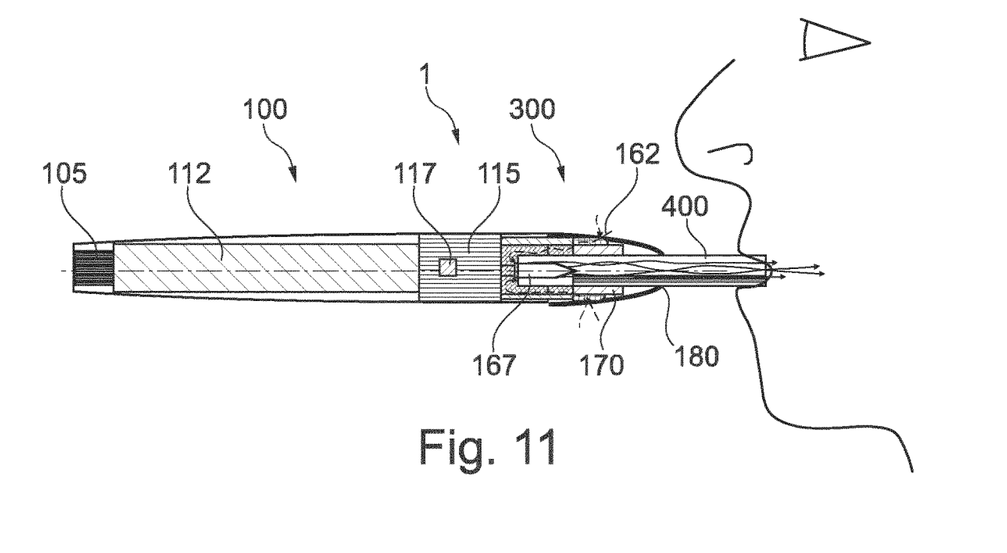
FIG. 11 shows schematically and exemplarily an embodiment of a holder according to the present disclosure.

FIG. 11 shows schematically and exemplarily another embodiment of a holder 1 according to the present disclosure in a cross section and with an aerosol generating article 400. As shown in FIG. 8, the holder 1 comprises a holding device 300 for the aerosol generating article 400 and a main unit 100. The holding device 300 is reversibly connected to the main unit 100. The main unit 100 comprises an electric power source 112 with a charging port 105. The aerosol generating article 400 is partially inserted into an opening 180 of the holding device 300 and gets penetrated by a heating element 167, which heats the aerosol generating article 400 to generate aerosol. Unlike the holder 1 given in the embodiment of FIG. 8, where the heating is achieved using an induction process, here resistive heating is used. The holding device 300 may also optionally comprise as in FIG. 8 a gyrosensor 117, a position control unit 115 and multi-terminal ring connector module 170. The position control unit 115 selects the first electrically conductive element 430 and the second electrically conductive element 440 out of the plurality of electrically conductive elements or tracks based on position data provided by the gyrosensor 117. An orientation of the holding device 300 with respect to the user's tongue may thereby decide which electrically conductive elements 430, 440 need to be active at a given moment.

Figure 12A:
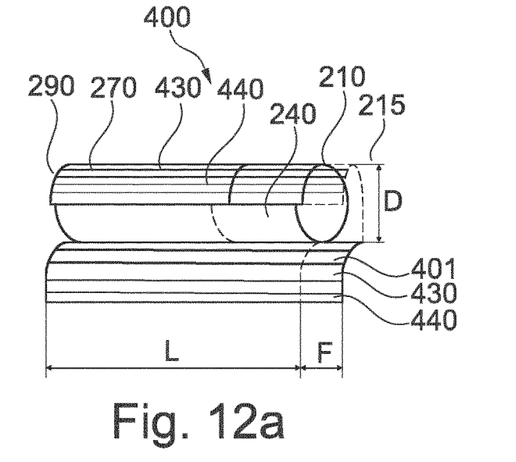
FIG. 12a shows schematically and exemplarily an embodiment of an aerosol generating article according to the disclosure.
Figure 12B:
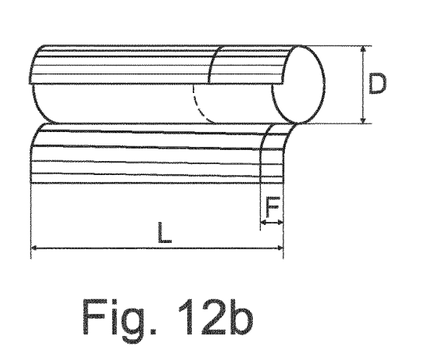
FIG. 12b shows schematically and exemplarily an embodiment of an aerosol generating article according to the disclosure.
Figure 12C:
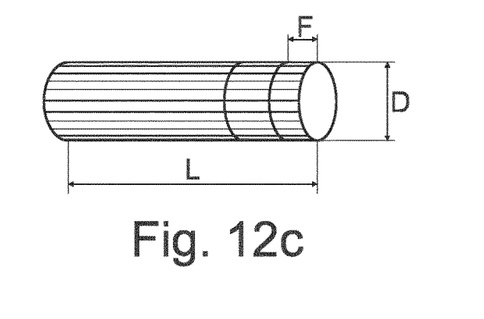
FIG. 12c shows schematically and exemplarily an embodiment of an aerosol generating article according to the disclosure.

FIGS. 12a to 12c show schematically and exemplarily another embodiment of an aerosol generating article 400 according to the disclosure. FIGS. 12a and 12b show the winding of a tipping paper 401, FIG. 12c shows a final form of the aerosol generating article 400. The aerosol generating article 400 comprises an aerosol forming substrate end 290, an aerosol forming substrate 270, a wrap paper 240, a plug 210, a plug end 215, and a tipping paper 401 with electrically conductive elements 430, 440. The plug 210 is wrapped with the tipping paper 401 at the plug end 215, which comes in contact with the tongue of the user. At the plug end 215, the tipping paper 401 extends forward relative to the plug 210. The tipping paper 401 is folded at the plug end 215, which touches the user's tongue, to keep a surface above the electrically conductive elements 430, 440 at the plug end 215 smooth to prevent wounds on the tongue of the user. 'F' represents a length of a folded area, 'D' represents a diameter of the aerosol generating article 400, and represents a length of the aerosol generating article 400.

For the purpose of the present description and of the appended claims, except where otherwise indicated, all numbers expressing amounts, quantities, percentages, and so forth, are to be understood as being modified in all instances by the term "about". Also, all ranges include the maximum and minimum points disclosed and include any intermediate ranges therein, which may or may not be specifically enumerated herein. In this context, therefore, a number A is understood as A±20% of A. Within this context, a number A may be considered to include numerical values that are within general standard error for the measurement of the property that the number A modifies. The number A, in some instances as used in the appended claims, may deviate by the percentages enumerated above provided that the amount by which A deviates does not materially affect the basic and novel characteristic(s) of the claimed disclosure. Also, all ranges include the maximum and minimum points disclosed and include any intermediate ranges therein, which may or may not be specifically enumerated herein.

Although illustrative examples of the present disclosure have been described above, in part with reference to the accompanying drawings, it is to be understood that the disclosure is not limited to these examples. Variations to the disclosed examples can be understood and effected by those skilled in the art in practicing the disclosure, from a study of the drawings, the specification and the appended claims.

In the claims, any reference signs placed between parentheses shall not be construed as limiting the claim. The term "comprising" does not exclude the presence of elements or steps other than those listed in a claim. The word "a" or "an" preceding an elements does not exclude the presence of a plurality of such elements. The disclosure can be implemented by means of hardware comprising several distinct elements. In the device claim enumerating several means, several of these means can be embodied by one and the same item of hardware. The mere fact that certain measured are recited in mutually different dependent claims does not indicate that a combination of these measure cannot be used to advantage.

The invention claimed is:

1. An aerosol-generating article for providing an electrical stimulation to a user, comprising:
    an aerosol-forming substrate;
    a first electrode;
    a second electrode;
    a first tipping paper; and
    a second tipping paper,
    wherein the first electrode is disposed at a first position of the aerosol-forming substrate and is configured to provide a first electrical contact to the user,
    wherein the second electrode is disposed at a second position at a front face of the aerosol-forming substrate and is configured to provide a second electrical contact to the user,
    wherein the second position is different from the first position to enable a provision of an electrical potential between the first electrode and the second electrode and to provide an electrical stimulation to the user,
    wherein the first electrode is accessible for a first region of the mouth, the first region of the mouth being a first area on a tongue of the user,
    wherein the second electrode is accessible for a second region of the mouth of the user, the second region being different from the first region,
    wherein the first electrode and the second electrode are electrically connectable to an electric power source to provide the electrical potential between the first electrode and the second electrode,
    wherein the first electrode is electrically connected to a first electrically conductive element extending at least partially along the aerosol-forming substrate,
    wherein the first electrically conductive element is electrically connected to a first electric terminal arranged at the aerosol-forming substrate,
    wherein the first electric terminal is electrically connectable to the electric power source,
    wherein the second electrode is electrically connected to a second electrically conductive element extending at least partially along the aerosol-forming substrate,
    wherein the second electrically conductive element is electrically connected to a second electric terminal arranged at the aerosol-forming substrate,
    wherein the second electric terminal is electrically connectable to the electric power source,
    wherein the first electric terminal and the second electric terminal are arranged on the first tipping paper,
    wherein the first electrically conductive element and the second electrically conductive element are arranged in the second tipping paper, and wherein the first tipping paper and the second tipping paper are wound together in an overlapping manner such that the first electric terminal electrically contacts the first electrically conductive element and the second electric terminal electrically contacts the second electrically conductive element.

2. The aerosol-generating article according to claim 1, wherein the first electrode is also at the front face of the aerosol-forming substrate.

3. The aerosol-generating article according to claim 1, wherein the first electrode is disposed on a lateral surface of the aerosol-forming substrate.

4. The aerosol-generating article according to claim 1, wherein the second region of the mouth is a lip of the user or a second area on the tongue of the user.

5. A holder, comprising:
an aerosol-generating article according to claim 1; and
a holding device comprising a reception portion, a first electric portion, and a second electric portion,
wherein the reception portion is configured to receive the aerosol-generating article,
wherein the first electric portion and the second electric portion are arranged in the reception portion to electrically contact a first electrode and second electrode of the aerosol-generating article, and
wherein the aerosol-generating article is partially inserted into the reception portion of the holding device.

6. The holder according to claim 5, wherein the first electric portion and the second electric portion are in electric connection with an electric power source.

7. The holder according to claim 5, wherein the holding device further comprises a heating element configured to heat the aerosol-generating article.

8. The holder according to claim 5, wherein the holding device further comprises a temperature control element, which is arranged at the reception portion and is configured to control a heat transfer between the reception portion, the first and the second electric portions, and the first and the second electrodes of the aerosol-generating article.

9. The holder according to claim 8, wherein the temperature control element is in contact with a housing of the holding device and is configured to transfer heat from the reception portion via the housing of the holding device to the environment.

* * * * *